United States Patent [19]

Bronkhorst

[11] 4,351,324
[45] Sep. 28, 1982

[54] THERAPEUTIC WALKING DEVICE
[75] Inventor: Arie J. Bronkhorst, Abilene, Tex.
[73] Assignee: David L. Buhrmann, Abilene, Tex.
[21] Appl. No.: 243,182
[22] Filed: Mar. 12, 1981
[51] Int. Cl.³ .............................................. A61F 3/00
[52] U.S. Cl. ................................................ 128/80 J
[58] Field of Search .................. 128/80 R, 80 J, 83, 128/87 R, 581, 596, 614

[56] References Cited
U.S. PATENT DOCUMENTS 3,086,522  4/1963  Frohmader ......................... 128/80 J
3,171,407  3/1965  Rogers .............................. 128/80 J Primary Examiner—John D. Yasko
Attorney, Agent, or Firm—James E. Bradley

[57] ABSTRACT

A therapeutic walking device has features to aid sufferers from cerebral palsy in reducing the tendency to walk on the balls of the foot. The device includes a foot section and a calf section formed at a 90 degree angle. The foot section has a heel support and a toe support for supporting the heel and toes of the user. A recessed section separates the heel support and toe support and is spaced lower so as to prevent pressure from being exerted on the sole of the foot between the heel and toes. The leg section is strapped about the calf of the user's leg.

3 Claims, 2 Drawing Figures

THERAPEUTIC WALKING DEVICE

BACKGROUND OF THE INVENTION

This invention relates in general to therapeutic walking devices, and in particular to a therapeutic device for persons such as cerebral palsy victims that have tendencies to walk on their toes.

One problem facing persons such as children suffering from cerebral palsy is in learning to walk. Often these children have a tendency to walk on the toes of the foot. One reason is that in response to pressure on the sole of the foot, the brain signals the muscles in the back of the calf and on the bottom of the foot to contract. This causes the foot to bend downwardly from its normal walking position.

One therapeutic device used in the past comprises a wooden block about 1½ inches thick. The block is mounted to the sole of a conventional hightop shoe. The block has a recessed area between the toe and heel, and the sole of the shoe has been cut out in the same area. This device is not very successful.

Another type of device is basically a brace for the ankle and foot. It is a fairly rigid plastic member that extends up the calf of the leg and has straps for strapping to the calf. A lower portion extends forwardly at 90 degrees for location below the sole of the foot. This device is not very successful either.

SUMMARY OF THE INVENTION

The therapeutic device disclosed in this application includes a leg section or brace that extends upwardly for strapping to the calf of the user's leg. A foot section extends forwardly from the leg section at 90 degrees for location below the user's foot. The foot section has a heel portion and a toe portion. These portions are separated by a recessed area. Straps are used to fasten the foot portion about the user's foot.

DESCRIPTION OF THE PREFERRED EMBODIMENT

Figure 1:
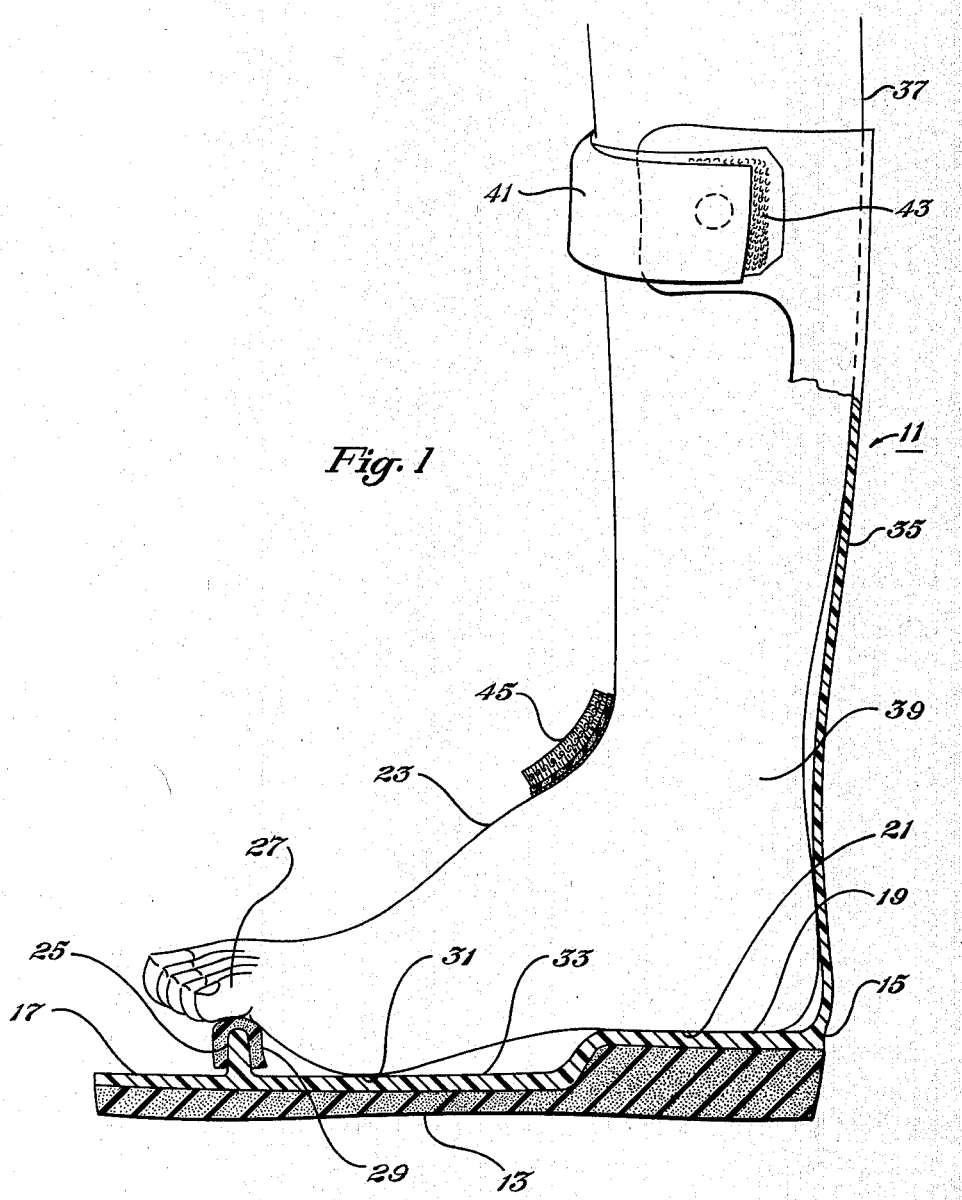
FIG. 1 is a vertical sectional view of a therapeutic walking device constructed in accordance with this invention.

Referring to FIG. 1, the therapeutic device 11 includes a sole 13 of a soft cushioning material such as neoprene rubber. Sole 13 has a flat bottom and an outer perimeter in the shape of a conventional shoe. An ankle foot brace 15 is mounted to the top of sole 13. Ankle foot brace 15 is of a single molded piece of fairly stiff and resilient material such as polypropolene. Brace 15 includes a foot section 17. Foot section 17 is bonded by adhesive to the top of the sole 13, defining a platform with an open top.

The rearward portion of foot section 17 is molded at a higher level than the forward portion. The rearward portion of sole 13 is about twice as thick as the forward portion. The rearward portion of foot section 17 is bonded to the thicker portion of sole 13, defining together a heel section 19. Heel section 19 has a flat upper surface for supporting the heel 21 of the foot 23 of the user. The forward edge of heel section 19 terminates at the forward edge of the user's heel 19. The total thickness of the heel section from the bottom of platform 13 to the top of heel section 19 is about 1½ inch.

A toe bar 25 is located in the forward portion of the foot section 17. Toe bar 25, as shown also in FIG. 2, extends transversely across the full width of the foot section 17 and is slightly curved to conform to the contour of the user's toes 27. A layer of cushioning 29 is placed on top of the toe bar 25. Toe bar 25 is positioned so that the phalanges or toe bones of the user will be located on top of the bar 25. The metatarsal head or ball 31 of the user's foot will be located directly rearward of toe bar 25. The longitudinal length of the toe bar 25 from the rearward side to the forward side is fairly short, giving the toe bar the shape of a berm. This causes the toes 27 to protrude forwardly past the toe bar 25.

In the preferred embodiment, the longitudinal length of toe bar 25, including the layer of cushioning 29, is about ½ inch. The height of toe bar 25 is selected so that it will be about the same height as heel section 19. In the preferred embodiment, the distance from the bottom of platform 13 to the top of cushioning layer 29 is about 1¼ inches.

The elevated heel section 19 and upwardly protruding toe bar 25 define a recessed section 33 between them. The heights of the heel section 19 and toe bar 25 are selected so that very little, if any, pressure will be applied to the ball 31 of the foot while the user is standing. In fact, although the ball 31 is shown in contact with the top of recessed section 33, in many cases, there is no contact whatsoever. In the preferred embodiment, the top of toe bar 25 is ½ inch above recessed section 33 or ⅝ inch if cushioning 29 is included. Heel section 19 is ¼ to ⅜ inch above recessed section 33.

Figure 2:
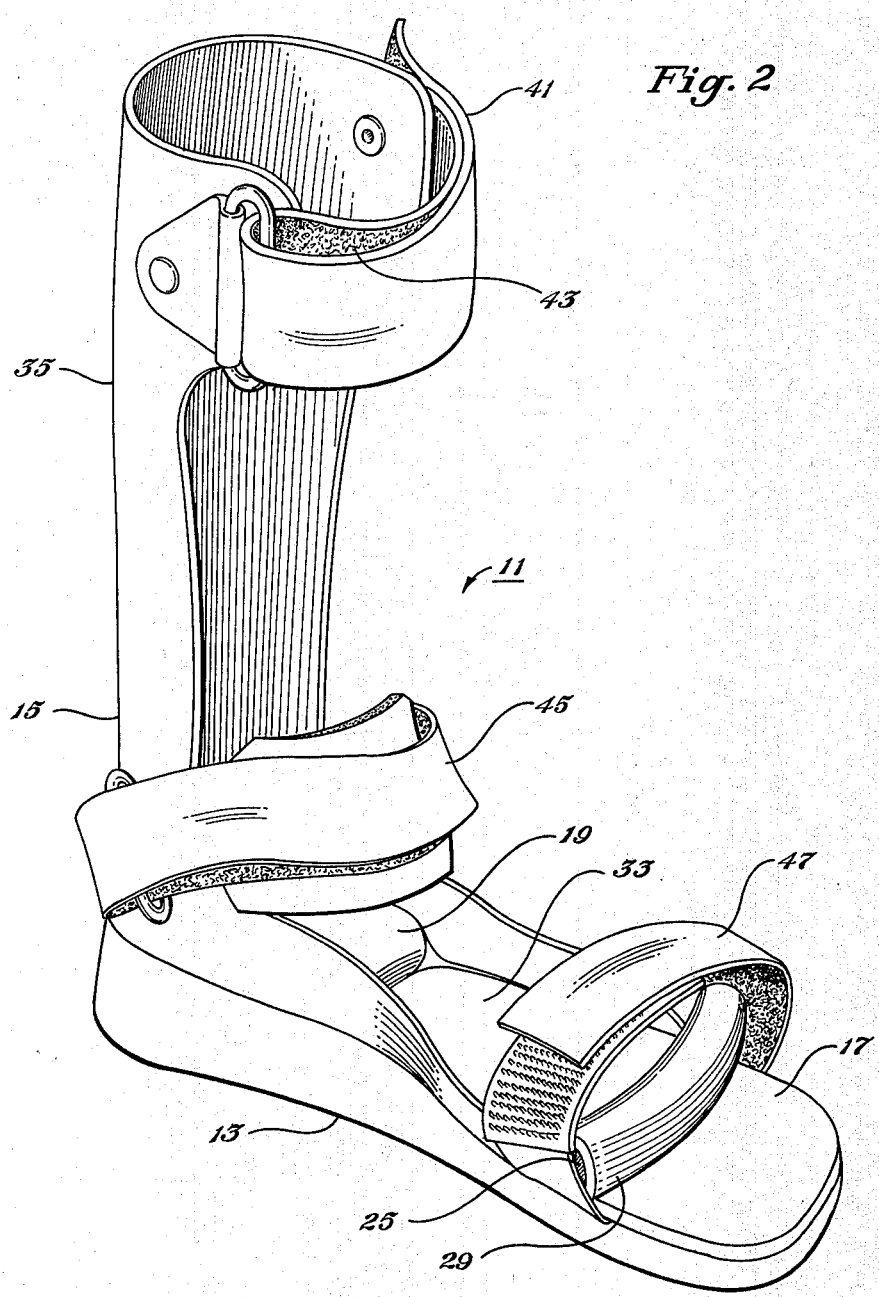
FIG. 2 is a perspective view of the device of FIG. 1.

Brace 15 includes a leg section 35 that is formed integrally with foot section 17 and extends upwardly at a 90 degree angle with respect to foot section 17. Leg section 35 fits about the user's calf 37 at a point above the ankle area 39 of the user's foot and below the user's knee. Referring to FIG. 2, the leg section 35 is in the shape of a channel with a rearward sidewall and an open front. The channel extends circumferentially about 120 degrees and is contoured for the shape of the user's leg.

Referring still to FIG. 2, a top strap 41 is located at the top of the leg section 35. Strap 41 may be of various types and is shown having Velcro material 43 on one side for tightly fastening the leg section 35 to the calf 37. An ankle strap 45, also having Velcro securing material, is located at the junction of the leg section 35 and foot section 17 for tightening about the user's ankle 39. A toe strap 47, also having Velcro securing material, is located near toe bar 25 for tightening the forward portion of the foot section 17 about the user's toes.

In operation, the user's foot 23 is placed into device 11, with the user's heel 21 in contact with the heel section 19 and the user's toes 27 resting on toe bar 25. Straps 41, 45 and 47 are tightly secured. When the user stands up, the ball 31 of the foot will either not contact at all, or will only slightly contact the recessed section 33. The lack of pressure on the user's sole between the heel 21 and toes 27 helps to reduce the stimulus to the brain to signal the plantar flexors to contract.

The plantar flexors are muscles that extend from the calf of the leg 37 down into the bottom of the foot 23. In addition, the leg section 35 restrains any tendency for the user to point his foot downwardly as the muscles involuntarily contract. The user initially will use the device only a few minutes a day, and will gradually use the device up to 8 or 10 hours a day. If desired, the device can be placed inside a rubber boot for use outside. This therapy causes the plantar flexors to stretch. Also, the therapy may cause the brain to gradually cease signaling the plantar flexors to contract because of pressure on the sole of the foot. After a period of time, the tendency for walking on the toes can be reduced sufficiently to cease using the device.

The invention has significant advantages. It provides therapy for persons suffering from illnesses such as cerebral palsy, allowing them to eventually overcome the tendency to walk on the toes or balls of the foot. The device is simple in construction and sufficiently comfortable to allow the user to use it in his normal activities.

While the invention has been shown in only one of its forms, it should be apparent to those skilled in the art that it is not so limited but is susceptible to various changes and modifications without departing from the spirit of the invention.

I claim:

1. A therapeutic walking device, comprising:
   a platform having a lower surface that is generally flat;
   the platform having an upper surface that includes a toe section having the shape of a berm protruding upwardly from the platform near the forward end of the platform and extending transversely across the platform for supporting the toes of the user;
   the platform having a heel section protruding upwardly from the platform at the rearward end for supporting the heel of the user, the forward end of the heel section being spaced from the rearward end of the toe section, defining a recessed section between the toe section and heel section for reducing pressure on the user's sole between the toes and heel while standing;
   a channel shaped leg section extending upwardly from the rearward end of the heel section for positioning against the rearward side of the calf of the user; and
   securing means for removably securing the device to the foot and calf of the user.

2. The device according to claim 1 wherein the securing means comprises:
   a top strap secured to the top of the leg section for tightening the leg section to the user's calf;
   an ankle strap secured to the device in the area where the user's ankle is located for tightening about the user's ankle; and
   a toe strap secured to the platform at the toe section for tightening the forward end of the user's foot to the device.

3. The device according to claim 1 wherein the platform has an open top, and wherein the leg section is open on its forward side.

* * * * *